United States Patent [19]

Ripley

[11] 4,044,066
[45] Aug. 23, 1977

[54] NICKEL-PHOSPHORUS OXIDATIVE DEHYDROGENATION CATALYST

[75] Inventor: Dennis L. Ripley, Bartlesville, Okla.

[73] Assignee: Phillips Petroleum Company, Bartlesville, Okla.

[21] Appl. No.: 620,729

[22] Filed: Oct. 8, 1975

Related U.S. Application Data

[62] Division of Ser. No. 140,963, May 6, 1971, Pat. No. 3,943,068.

[51] Int. Cl.$^2$ ............................................. C07C 11/12
[52] U.S. Cl. ............................. 260/680 E; 252/437; 260/683.3
[58] Field of Search ............ 260/680 R, 680 E, 683.3; 252/437, 472, 477 Q

[56] References Cited

U.S. PATENT DOCUMENTS

| | | | |
|---|---|---|---|
| 2,926,207 | 2/1960 | Folkiws | 252/437 |
| 2,945,900 | 7/1960 | Alexandria et al. | 260/680 E |
| 3,270,080 | 8/1966 | Christmann | 260/680 E |
| 3,308,188 | 3/1967 | Bajars | 260/683.3 |
| 3,409,701 | 11/1968 | Noddings et al. | 260/683.3 |
| 3,538,019 | 11/1970 | Capik et al. | 252/437 |
| 3,709,951 | 1/1973 | Hutson, Jr. et al. | 260/680 E |
| 3,766,191 | 10/1973 | Cichowski | 260/680 E |

*Primary Examiner*—Oscar R. Vertiz
*Assistant Examiner*—Gary P. Straub

[57] ABSTRACT

Organic compounds are dehydrogenated to compounds having a higher degree of unsaturation by contacting the feedstock in the vapor phase at an elevated temperature in the presence of an oxygen-containing gas with a catalyst containing nickel in combination with phosphorus and oxygen. The nickel-phosphorus-oxygen catalysts are particularly characterized in that they contain from 0.1 to 16.8 weight percent phosphorus, based on the weight of the nickel-phosphorus-oxygen catalyst. Representative of such conversions is the oxidative dehydrogenation of butane to 1,3-butadiene. The conversion products are valuable compounds particularly useful as intermediates for the preparation of polymeric materials such as synthetic rubbers and the like.

8 Claims, No Drawings

NICKEL-PHOSPHORUS OXIDATIVE DEHYDROGENATION CATALYST

This is a division of application Ser. No. 140,963, filed May 6, 1971, now U.S. Pat. No. 3,943,068, issued Mar. 9, 1976.

The present invention relates to chemical compositions. More particularly, the invention relates to catalyst compositions, their preparation and to catalytic processes employing such compositions, e.g., processes for effecting the dehydrogenation of hydrocarbons.

Thermal catalytic and noncatalytic processes for converting organic compounds to compounds having a higher degree of unsaturation are known. The former are characterized by undesirable side reactions, low order of conversion and yields, and poor product selectivity. The catalytic processes are generally characterized by the particular catalytic material employed and the conditions under which the processes are operated, e.g., in the absence or presence of oxygen. While a number of such catalytic processes have attained some measure of commercial success, there is a continuing search to develop catalytic materials for such processes. Desirable catalysts are those materials which are more efficient in minimizing side reactions, in improving conversion rates, in improving yields and selectivities to desired end product, which have a low susceptibility to deactivation, i.e., are capable of extended periods of operation without regeneration, and which can be readily regenerated when necessary to an activity approaching that of fresh catalyst. The problem constantly faced by those skilled in the art is the discovery and characterization of the compositions which are highly efficient dehydrogenation catalysts.

A number of catalysts and catalyst systems which include halogens or halogen-releasing compounds have been disclosed. These, however, have exhibited so many disadvantages in regard to equipment corrosion and the additional expense of continuously feeding, recovering and recycling the relatively expensive halogen materials that economically large scale use of such catalytic materials has been precluded. Halogen-free catalysts are the most desirable for use in dehydrogenation processes.

The present invention provides a novel catalyst and a novel process for the conversion of dehydrogenatable organic feedstocks to products having a greater degree of unsaturation and which have the same or lower number of carbon atoms as in the hydrocarbon feed. According to this invention, organic feedstocks can be converted to products having a greater degree of unsaturation by contacting said feedstock under dehydrogenation conditions in the vapor phase in the presence of molecular oxygen with a calcined catalytic material comprising phosphorus, nickel and oxygen. Hydrocarbon feeds are particularly applicable. Thus, paraffinic hydrocarbons can be converted in good yields to diolefins and/or monoolefins and monoolefins can be converted to diolefins. The invention is particularly applicable for the production of diolefins from paraffins and particularly useful results are obtained by the dehydrogenation of butane to 1,3 -butadiene.

The hydrocarbon feedstocks which are applicable for the oxidative dehydrogenation processes of the present invention comprise dehydrogenatable aliphatic hydrocarbons having from about 2 to about 12 carbon atoms per molecule and at least one

grouping. These can be branched or unbranched and include paraffins as well as monoolefins, but paraffins are presently preferred. Particularly preferred as feed materials are dehydrogenatable aliphatic hydrocarbons having from about 4 to about 8 carbon atoms per molecule. The conversion of butane has been found particularly advantageous by the process of the invention. Some specific example of other feeds include isobutane, pentane, methylbutanes, hexane, 2 -methylhexane, octane, 2,4 -dimethyloctane, butene-2, 2 -methylbutene-1, hexene-2, octene-1, 3 -methylnonene-4, and the like, including mixtures of such compounds.

The novel catalysts of the present invention comprise phosphorus in association with nickel. These elements are not in the elemental state but are combined with sufficient oxygen to form one or more neutral compounds, for example, mixtures of nickel oxide, nickel phosphate and phosphorus oxide. A particular feature of these catalysts is the criticality which exists between the amount of nickel and phosphorus. Thus, while the catalysts of this invention must contain phosphorus and nickel in association with oxygen, it is particuarly critical that the amount of phosphorus in the catalysts of this invention be present in at least a finite amount but less than that required for stoichiometric nickel phosphate formation. Thus, as a convenience, the catalysts prepared according to the present invention can be viewed as mixtures of nickel oxide and nickel phosphate, although the exact manner in which these elements are combined within the catalyst is not known with certainty.

Generally, catalysts of this invention, when substantially only nickel, phosphorus and oxygen are present, will contain from about 0.1 to about 16.8 weight percent phosphorus and from about 48 to about 75 weight percent nickel, the remainder being oxygen in amounts sufficient to satisfy the valence requirements of both nickel and phosphorus. Preferentially, the catalyst will contain from about 1 to about 15 weight percent phosphorus with a particularly desirable range being from about 2 to 12 percent phosphorus.

Optionally, the above catalyst is supported on or diluted with a conventional catalytic support material. The presently preferred support material is a catalytic grade silica, alumina, boria, titania, zirconia or silica-alumina. The support material, when used, will comprise about 10 to about 90, preferably from about 30 to about 60, weight percent of the total catalyst composition.

The above-described catalytic composition can still further, optionally, be associated with a catalyst-modifying quantity of other metals or metal oxides which can improve its activity, selectivity, or stability. For example, the catalyst can contain minor amounts of a Group IA or a Group IIA metal. When present, the alkali or alkaline earth metal, preferably an alkali metal, will be present in the catalytic composition in the range of from about 0.1 to about 10 weight percent, preferably 0.1–4 weight percent, based upon the weight of the above-described catalyst composition. The addition of minor amounts of tin has also been found to be beneficial. When significant amounts of elements other than nickel, phosphorus or oxygen are present in the catalyst, the proportions of phosphorus and nickel in the invention catalyst can be conveniently described in terms of the atomic ratio of phosphorus to nickel. Sufficient phosphorus is generally present in the catalyst such that the phosphorus:nickel atomic ratio is in the range of from about 0.1:1 to about 0.65:1.

The catalyst of the present invention can be prepared by any suitable method. Conventional methods such as coprecipitation, impregnation, or dry mixing can be used. In general, any method can be used which will provide a composition containing the above-described elements in the above-described proportions and which will have a catalytic surface area of at least one square meter per gram.

Thus, a phosphorus compound and a compound of nickel are combined in any suitable way. Substantially any phosphorus compound or any nickel compound can be employed in the catalyst composition so long as none of the compounds are deleterious to the final dehydrogenation catalyst and essentially all of the elements in the compounds used, other than the phosphorus, nickel, and oxygen, and other than elements which can contribute to the effectiveness of the catalyst, are removed from the final catalyst by prior washing or by volatilization.

It has been found that, in some instances, minor amounts of still other elements can be tolerated in the catalyst. For example, when nickel is incorporated into the catalyst by way of the nickel sulfate compound, minor amounts of residual sulfur can be found in the finished catalyst, and the catalyst can still be effective. On the other hand, halogen residues are generaly undesirable in such catalysts. Therefore, when halide compounds are used in the preparation of the catalyst, it is generally advisable to substantially remove the halogen residues such as by sufficient washing at an appropriate point in the preparation procedure.

Suitable phosphorus compounds include any compound which is soluble or dispersible in water. Examples of such compounds include phosphorus halides, phosphorus oxides, ammonium phosphate, alkali metal phosphates, alkaline earth phosphates, and the like, including mixtures thereof.

Similarly, suitable nickel compounds can be used. These can include both organic or inorganic compounds. Some examples of these are nickel oxide, nickel acetylacetonate, nickel nitrate, nickel acetate, nickel sulfate, nickel chloride, and the like, including mixtures thereof. Similarly, examples of catalyst-modifying materials comprising one or more alkali or alkaline earth metal compounds can include lithium nitrate, sodium carbonate, potassium chloride, rubidium acetate, cesium nitrate, magnesium bromide, calcium chloride, strontium tartrate, sodium phosphate, and the like, including mixtures thereof.

A convenient preparation is to precipitate suitable catalyst-forming compounds from aqueous solutions followed by conventional aging, washing, drying, calcining, pelletizing, and the like. To these compositions, either in the wet gel, dry gel, or even calcined states, can be mixed or added by impregnation other beneficial metals or even additional amounts of suitable phosphorus or nickel compounds.

When a catalyst support is used, it can conveniently be introduced during the coprecipitation stage of the catalyst preparation. Alternatively, a solid catalyst support, generally in the finished form of a pellet, sphere, or particle, can be impregnated with solutions of a phosphorus compound and of a suitable nickel compound. The impregnated solid can then be dried and calcined. When other catalyst-modifying agents are used, they can be introduced into the catalyst either before, during or after the phosphorus and the nickel compounds have been associated with the support.

Whichever catalyst preparation technique is used, the catalyst is activated prior to contact with the feed hydrocarbon by a calcination step. Thus, the finished catalyst is calcined in an oxygen-containing gas such as air at a temperature in the range of from about 900° to about 1500° F. For a time in the range of about 1 to about 24 hours, or until the catalyst is active for carrying out the oxidative dehydrogenation step.

The hydrocarbon feedstocks can be dehydrogenated according to the processes using the catalyst of the present invention at temperatures in the range of from about 800° to about 1300° F., preferably from about 950° to about 1100° F., at any convenient pressure such as from about 7 to about 250 psia, and at a hydrocarbon-oxygen ratio of from about 1:0.5 to about 1:4. The presence of steam is frequently beneficial and a steam:hydrocarbon ratio up to about 50:1 can be used. The hydrocarbon feed rate will generally be in the range of about 50 to about 800 GHSV. The fixed catalyst bed is the preferred mode of contact, but other modes, such as a fluidized, bed, can also be used.

The hydrogenation processes of this invention are ordinarily carried out by forming a mixture, preferably preheated, of hydrocarbon feed, the oxygen-containing gas, and the steam (when used) and passing this mixture over the catalyst at the selected temperature. The effluent from the reaction zone is subjected to any suitable separation method to isolate and recover the desired products. Unconverted feeds or partially converted material can be recycled.

Generally, at least trace amounts of oxygenated products are also formed in these reactions. For example, compounds such as furan, acetaldehyde, furfural and acetic acid can be obtained depending upon the feed. In some instances, butadiene can be formed as a by-product of the oxidative dehydrogenation of isopentane to isoprene.

The catalyst can operate for long periods without regeneration. However, if and when regeneration is required, this can be accomplished by simply halting the flow of feed hydrocarbons. Contact of the catalyst with the air and steam can be maintained at the elevated temperature until sufficient activity is restored.

The invention can be illustrated by the following examples.

EXAMPLE 1

Preparation of Catalysts

Catalyst A: 7.43 g of $NH_4H_2PO_4$ and 159.1 g of $NiSO_4 \cdot 6H_2O$ were each dissolved in distilled and deionized water, then mixed together. Aqueous NaOH was then slowly added with stirring until precipitation was complete and the mixture was slightly basic. The precipitate was filtered, wash with 500 cc water, refiltered, dried and calcined at 1000° F. for 16 hours. The solid Ni/P/O catalyst, containing 3.2 weight percent P, was then ground and screened to 20/30 mesh.

Catalyst B: Using 22.3 g $NH_4H_2PO_4$ and 127.5 g $NiSO_4 \cdot 6H_2O$, the same procedure of Catalyst A was used to produce a Ni/P/O catalyst containing 8.2 weight percent P.

Catalyst C: In a maner similar to the above, 22.3 g $NH_4H_2PO_4$ and 127.5 g $NiSO_4.6H_2O$ were each dissolved in distilled and deionized water, then mixed and precipitated by the addition of $NH_4OH$ until the mixture was slightly basic. The precipitate was filtered, washed refiltered, dried and calcined at 1000° F. for 16 hours. The resulting solid catalyst was essentially nickel phosphate, containing 16.9 weight percent P, and was ground and screened to 20/30 mesh.

Catalyst D: 7.43 g of $NH_4H_2PO_4$ and 159 g $NiSO_4.6H_2O$ were dissolved in distilled water to give 500 cc solution having a pH of about 3. Sufficient NaOH solution was then added to increase the pH to about 9.5. The resulting precipitate was filtered, washed twice with 700 cc distilled water and allowed to stand in a third wash for about 16 hours. The precipitate was again filtered, yielding 344 g wet gel which was divided into three portions of about 114 g each. One portion was dried and calcined at 1100° F. for 3 hours. The solid Ni/P/O catalyst, containing 3.2 weight percent P, was ground and screened to 20/40 mesh.

Catalyst E: The second 114 g portion of the wet gel from the preparation of Catalyst D was mixed with 8.5 g of $H_3PO_4$ (85 percent), then treated as Catalyst D to yield a Ni/P/O catalyst containing 12.7 weight percent P.

Catalyst F: The third 114 g portion of the wet gel from the preparation of Catalyst D was mixed with 17.0 g $H_3PO_4$ (85 percent), then treated as Catalyst D to yield a Ni/P/O catalyst containing 18.1 weight percent P.

Catalyst G: 232 g $NiSO_4.6H_2O$ was dissolved and diluted to 600 cc with distilled water, and 105 g KOH (85 percent) was dissolved and diluted to 800 cc. These two solutions were added simultaneously and dropwise into 200 cc distilled water maintaining about a pH of 8. About 675 cc of the KOH solution was used with a final pH of 8.3. The precipitate was filtered, washed with 1000 cc distilled water, refiltered, washed with another 1000 cc water, refiltered, washed with 200 cc water, refiltered recovering 458 g wet gel. One 114 g portion of the wet gel was mixed with 2.6 g $H_3PO_4$ (85 percent), then dried, and calcined 3 hours at 1100° F., then ground and screened to 20/40 mesh. The catalyst contained 3.3 weight percent P and about 1.7 weight percent K.

Catalyst H: Another 114 g portion of the wet gel from the preparation of Catalyst G was mixed with 4.0 g $H_3PO_4$ (85 percent), then treated as Catalyst G yielding a catalyst containing 4.9 weight percent P and about 1.7 weight percent K.

Catalyst I: The remaining wet gel from Catalyst G was washed again with 475 cc water and refiltered yielding 208 g wet gel. A 104 g portion of the wet gel was mixed with 2.6 g $H_3PO_4$ (85 percent), then treated as was Catalyst G yielding a catalyst containing 3.5 weight percent P and about 0.4 weight percent K.

Catalyst J: The remaining 104 g portion of wet gel from the preparation of Catalyst I was mixed with 4.0 g $H_3PO_4$ (85 percent) and then treated as was Catalyst G yielding a catalyst containing 5.1 weight percent P and about 0.4 weight percent K.

EXAMPLE II

Oxidative Dehydrogenation of Butane

The above-described catalyst were charged into a fixed bed reactor and used in several runs in which butane was dehydrogenated in the presence of air and steam. The run conditions were 100 GHSV of butane and 500 GHSV air with steam:hydrocarbon ratios and temperatures as shown in the following Table I with results, after ¼ hour, of these runs:

TABLE I

| Run | Catalyst | % P | Steam:-Hydrocarbon Ratios | Conversion/Modivity[1] 1000° F. | 1100° F. | 1200° F. |
|---|---|---|---|---|---|---|
| 1 | A | 3.2 | 22.9:1 | 42.3/60.5 | 48.5/63.9 | 47.3/59.2 |
| 2 | B | 8.2 | 22.1:1 | 14.3/70.3 | 23.9/69.8 | 43.4/67.2 |
| 3 | C | 16.9 | 30.4:1 | 0/0 | 5.2/84.8 | 20.5/72.8 |

[1]Modivity is a simplified selectivity based on analysis of gas phase products for converted hydrocarbons, carbon oxides and unconverted feed. As used herein and in the following examples, conversions/yields are reported on same basis as modivity.

The data in table I show that the Ni/P/O catalysts of invention Runs 1 and 2 show substantial activity for the oxidative dehydrogenation of butane to form olefins and diolefins. Control Run 3, in which the phosphorus content is outside the scope of the invention shows substantially poorer activity, and actually no activity at 1000° F.

In Table II below, the products of invention Run 1 are shown in greater detail.

TABLE II

| Temp. °F. | Conv., % | Modivity, %[2] | Butadiene | Butenes | Cracked | Oxidized |
|---|---|---|---|---|---|---|
| 1000 | 42.3 | 55.5 | 12.7 | 10.8 | 5.0 | 13.8 |
| 1100 | 44.7 | 53.0 | 11.0 | 12.7 | 9.5 | 11.5 |
| 1200 | 46.5 | 44.0 | 12.5 | 8.4 | 12.2 | 13.4 |

[2]To butenes and butadiene only. Modivity is a modified selectivity based on analysis of gas phase products for converted hydrocarbons, oxides of carbon and unconverted feed.

The data in Table II show that a significant amount of butadiene was produced in the invention run.

EXAMPLE III

Other catalysts of the invention were used in the oxidative dehydrogenation of butane to butadiene and other olefinic products. These runs are shown in Table III which includes the essential conditions as well as the results of the runs. For still another comparison, the table includes one more catalyst (Catalyst F) which is outside the scope of the invention.

TABLE III

| Run | Catalyst | % P | Steam:-Hydrocarbon Ratios | C4 GHSV | Air GHSV | Temp., °F. | Time, Hrs. | Conv., % | Modivity[1] | Butadiene | Butenes | Cracked | Oxidized |
|---|---|---|---|---|---|---|---|---|---|---|---|---|---|
| 4 | D | 3.6 | 5:1 | 300 | 1500 | 1050 | 0.25 | 20.7 | 49.8 | 6.8 | 3.5 | 2.5 | 8.0 |
| 5 | E | 12.7 | 5:1 | 300 | 1500 | 1050 | 0.25 | 8.2 | 75.3 | 3.9 | 2.3 | 1.2 | 0.8 |
| 6 | D | 3.6 | 9.8:1 | 150 | 1500 | 1050 | 0.25 | 31.8 | 32.8 | 7.3 | 3.1 | 3.0 | 18.3 |
| 7 | E | 12.7 | 9.8:1 | 150 | 1500 | 1050 | 0.25 | 27.4 | 33.8 | 8.7 | 0.6 | 2.7 | 15.4 |
| 8 | F | 18.1 | 9.8:1 | 150 | 1500 | 1050 | 0.25 | 2.2 | 43.5 | 0.0 | 0.9 | 1.2 | 0.0 |
| 9 | G[3] | 3.3 | 11:1 | 500 | 1500 | 1100 | 12 | 25.9 | 48.3 | 8.7 | 3.8 | 2.6 | 10.8 |
| 10 | I[2] | 3.5 | 11:1 | 500 | 1500 | 1100 | 12 | 30.0 | 36.7 | 9.3 | 1.7 | 2.2 | 16.8 |

TABLE III-continued

| Run | Catalyst | % P | Steam:-Hydrocarbon Ratios | C₄ GHSV | Air GHSV | Temp., °F. | Time, Hrs. | Conv., % | Modivity[1] | Yields | | | |
|---|---|---|---|---|---|---|---|---|---|---|---|---|---|
| | | | | | | | | | | Butadiene | Butenes | Cracked | Oxidized |
| 11 | H[3] | 4.9 | 11:1 | 500 | 1500 | 1100 | 12 | 26.8 | 41.8 | 8.9 | 2.3 | 2.8 | 12.8 |
| 12 | J[2] | 5.1 | 11:1 | 500 | 1500 | 1100 | 12 | 27.3 | 40.8 | 8.6 | 2.5 | 2.5 | 13.7 |

[1]To butadiene and butenes. Modivity is a modified selectivity based on analysis of gas phase products for converted hydrocarbons, oxides of carbon and unconverted feed.
[2]Also contains about 0.4 weight percent K.
[3]Also contains about 1.7 weight percent K.

The data in Table III show that the catalysts of the present invention are active for promoting the oxidative dehydrogenation of butane to substantial amounts of butadiene over a wide range of operating conditions. The catalyst of control Run 8 is still another showing that if the phosphorus content of a Ni/P/O catalyst is excessive the catalyst is largely, if not completely, inactivated.

While certain embodiments of the invention have been described for illustrative purposes, the invention is not limited thereto. Various other modifications or embodiments of the invention will be apparent to those skilled in the art in view of this disclosure. Such modifications or embodiments are within the spirit and scope of the disclosure.

I claim:

1. A process for the dehydrogenation of a hydrocarbon feedstock having 2 to 12 carbon atoms and at least one

grouping which comprises contacting said feedstock in the vapor phase under dehydrogenation conditions in the presence of molecular oxygen with a catalyst consisting essentially of nickel, phosphorus, an alkali metal and oxygen, wherein the amount of nickel is in the range of 48 to 75 weight percent, the amount of phosphorus is in the range of 0.1 to 16.8 weight percent, the amount of alkali metal is in the range of about 0.1 to 10 weight percent and the amount of oxygen is sufficient to satisfy the valence requirements of all elements therein present; and wherein the amount of phosphorus is less than that required for stoichiometric nickel phosphate.

2. A process according to claim 1 wherein the amount of phosphorus is in the range of 1–15 weight percent.

3. A process according to claim 1 wherein the amount of phosphorus is in the range of 2–12 weight percent.

4. A process according to claim 1 wherein the phosphorus:nickel atomic ratio is in the range of 0.1–0.65:1.

5. A process according to claim 1 wherein said catalyst is in combination with a catalytic carrier material selected from the group consisting of boria, titaniam, zirconia, silica, alumina or silica-alumina.

6. A process according to claim 5 wherein said carrier material comprises from 10 to 90 weight percent of total catalyst composition.

7. A process according to claim 1 wherein said feedstock comprises a paraffinic hydrocarbon.

8. A process according to claim 7 wherein said hydrocarbon feedstock comprises butane.

* * * * *